United States Patent
Serhan et al.

(10) Patent No.: US 8,097,037 B2
(45) Date of Patent: Jan. 17, 2012

(54) METHODS AND DEVICES FOR CORRECTING SPINAL DEFORMITIES

(75) Inventors: Hassan A. Serhan, South Easton, MA (US); Michael A. Slivka, Taunton, MA (US)

(73) Assignee: DePuy Spine, Inc., Raynham, MA (US)

( * ) Notice: Subject to any disclaimer, the term of this patent is extended or adjusted under 35 U.S.C. 154(b) by 1194 days.

(21) Appl. No.: 11/613,221

(22) Filed: Dec. 20, 2006

(65) Prior Publication Data

US 2008/0154375 A1   Jun. 26, 2008

(51) Int. Cl.
*A61F 2/44* (2006.01)
*A61B 17/88* (2006.01)

(52) U.S. Cl. .................. 623/17.16; 623/17.11; 606/279

(58) Field of Classification Search .................. 606/246, 606/279; 623/17.11, 17.16
See application file for complete search history.

(56) References Cited

U.S. PATENT DOCUMENTS

| | | | |
|---|---|---|---|
| 5,133,719 A | 7/1992 | Winston |
| 5,342,365 A | 8/1994 | Waldman |
| 5,425,772 A | 6/1995 | Brantigan |
| 5,593,408 A | 1/1997 | Gayet et al. |
| 5,609,635 A | 3/1997 | Michelson |
| 5,669,909 A | 9/1997 | Zdeblick et al. |
| 5,683,463 A | 11/1997 | Godefroy et al. |
| 5,716,415 A | 2/1998 | Steffee |
| 5,766,252 A | 6/1998 | Henry et al. |
| 5,776,199 A | 7/1998 | Michelson |
| 5,782,919 A | 7/1998 | Zdeblick et al. |
| 5,888,224 A | 3/1999 | Beckers et al. |
| 5,888,227 A | 3/1999 | Cottle |
| 5,984,922 A | 11/1999 | McKay |
| 5,984,967 A | 11/1999 | Zdeblick et al. |
| 6,033,405 A | 3/2000 | Winslow et al. |
| 6,045,580 A | 4/2000 | Scarborough et al. |
| 6,093,207 A | 7/2000 | Pisharodi |
| 6,113,639 A | 9/2000 | Ray et al. |
| 6,117,174 A | 9/2000 | Nolan |
| 6,143,033 A | 11/2000 | Paul et al. |
| 6,165,219 A | 12/2000 | Kohrs et al. |
| 6,241,771 B1 | 6/2001 | Gresser et al. |
| 6,245,072 B1 | 6/2001 | Zdeblick et al. |
| 6,258,125 B1 | 7/2001 | Paul et al. |

(Continued)

FOREIGN PATENT DOCUMENTS

EP      1634549      3/2006

(Continued)

OTHER PUBLICATIONS

DePuy AcroMed Product Catalog, 13 pp., Lumbar I/F Cage Implants & Instruments, IF01-10-001 Sep. 1999.

(Continued)

*Primary Examiner* — Eduardo C Robert
*Assistant Examiner* — Ellen C Hammond
(74) *Attorney, Agent, or Firm* — Nutter McClennen & Fish LLP (57) ABSTRACT

Method and devices are provided for correction of spinal deformities. The methods and devices are particularly useful for correcting an abnormal curvature of the spine. In one exemplary embodiment, the methods and devices provide a spinal implant that can include a wedged-shape configuration. The wedged implant can be interposed between adjacent vertebrae that form part of an abnormal spinal curvature, thereby realigning the vertebrae and restoring the normal curvature to the spine.

23 Claims, 11 Drawing Sheets

U.S. PATENT DOCUMENTS

| | | | |
|---|---|---|---|
| 6,277,149 B1 | 8/2001 | Boyle | |
| 6,283,966 B1 | 9/2001 | Houfburg | |
| 6,302,914 B1 | 10/2001 | Michelson | |
| 6,315,795 B1 | 11/2001 | Scarborough et al. | |
| 6,325,827 B1 | 12/2001 | Lin | |
| 6,428,544 B1 | 8/2002 | Ralph et al. | |
| 6,436,101 B1 | 8/2002 | Hamada | |
| 6,520,993 B2 * | 2/2003 | James et al. | 623/17.16 |
| 6,530,955 B2 | 3/2003 | Boyle et al. | |
| 6,547,823 B2 * | 4/2003 | Scarborough et al. | 623/17.16 |
| 6,623,484 B2 * | 9/2003 | Betz et al. | 606/279 |
| 6,682,564 B1 | 1/2004 | Duarte | |
| 6,699,288 B2 | 3/2004 | Moret | |
| 6,843,804 B2 * | 1/2005 | Bryan | 623/17.11 |
| 7,105,023 B2 | 9/2006 | Eckman | |
| 2001/0049560 A1 | 12/2001 | Paul et al. | |
| 2002/0058950 A1 | 5/2002 | Winterbottom et al. | |
| 2002/0099377 A1 | 7/2002 | Zucherman et al. | |
| 2002/0111679 A1 | 8/2002 | Zucherman et al. | |
| 2002/0138078 A1 | 9/2002 | Chappuis | |
| 2004/0199251 A1 | 10/2004 | McCombe et al. | |
| 2004/0249461 A1 * | 12/2004 | Ferree | 623/17.11 |
| 2005/0010292 A1 * | 1/2005 | Carrasco | 623/17.11 |
| 2005/0071005 A1 | 3/2005 | Carli et al. | |
| 2005/0149192 A1 * | 7/2005 | Zucherman et al. | 623/17.11 |
| 2005/0261767 A1 * | 11/2005 | Anderson et al. | 623/16.11 |
| 2005/0273171 A1 * | 12/2005 | Gordon et al. | 623/17.15 |
| 2006/0217807 A1 | 9/2006 | Peterman et al. | |
| 2007/0050029 A1 * | 3/2007 | Carrasco | 623/17.11 |
| 2007/0093901 A1 * | 4/2007 | Grotz et al. | 623/17.11 |

FOREIGN PATENT DOCUMENTS

| | | |
|---|---|---|
| WO | WO-95/25487 | 9/1995 |
| WO | WO-2004/000176 | 12/2003 |

OTHER PUBLICATIONS

LifeNet Product Brochure, "VG2 Ramp Allograft" (LNPRO736), 4 pp., 2002.

* cited by examiner

FIG. 1A

CORONAL

SAGITTAL

METHODS AND DEVICES FOR CORRECTING SPINAL DEFORMITIES

FIELD OF THE INVENTION

The present invention relates to methods and devices for correcting spinal deformities.

BACKGROUND OF THE INVENTION

Spinal deformities, which include rotation, angulation, and/or curvature of the spine, can result from various disorders, including, for example, scoliosis (abnormal curvature in the coronal plane of the spine), kyphosis (backward curvature of the spine), and spondylolisthesis (forward displacement of a lumbar vertebra). Other causes of an abnormally shaped spine include trauma and spinal degeneration with advancing age. Early techniques for correcting such deformities utilized external devices that applied force to the spine in an attempt to reposition the vertebrae. These devices, however, resulted in severe restriction and in some cases immobility of the patient. Furthermore, current external braces have limited ability to correct the deformed spine and typically only prevent progression of the deformity.

More recent techniques for correcting spinal deformities utilize fusing of adjacent vertebrae through the disc space (the space previously occupied by the spinal disc interposed between the adjacent vertebrae), known as spinal fusion. Typically, a fusion cage and/or bone graft is placed into the disc space to position the vertebrae apart so as to create more space for the nerves, to restore the angular relationship between the adjacent vertebrae to be fused, and to provide for material that can participate in and promote the fusion process. While current spinal fusion techniques are effective, they typically require multiple levels of vertebrae to be fused.

Accordingly, there remains a need for improved methods and devices for correcting an abnormal spinal curvature.

SUMMARY OF THE INVENTION

The present invention generally provides methods and devices for correcting spinal deformities. In one embodiment, a method for correcting a spinal deformity is provided and includes inserting a spinal implant into a disc space formed between two adjacent vertebrae located along a curvature resulting from a deformity in a spinal column. The disc space can include a first lateral side located adjacent to a concave side of the curvature in the spinal column and a second lateral side located adjacent to a convex side of the curvature in the spinal column, and the spinal implant can have a wedge-shaped configuration with a first side having a height that is greater than a height of a second opposite side. The first side of the spinal implant can be positioned adjacent the first lateral side of the disc space such that a height of the first lateral side of the disc space is greater than a height of the second lateral side of the disc space. The second opposite side of the spinal implant can optionally be positioned adjacent the second lateral side of the disc space. In one exemplary embodiment, the spinal implant can have a footprint that substantially matches a footprint of the endplates of the adjacent vertebrae.

In another embodiment, the method can include inserting a second spinal implant into the disc space. The second spinal implant can have a wedge-shaped configuration with a first side having a height greater than a height of a second opposite side. The height of the first side of the second spinal implant can be less than the height of the first side of the first spinal implant. The second side of the second spinal implant can be positioned adjacent the second lateral side of the disc space.

In another embodiment, the spinal implant can have opposed posterior and anterior sides extending between the first and second sides, and the posterior side of the spinal implant can have a height greater than a height of the anterior side such that a height of a posterior side of the disc space is greater than a height of an anterior side of the disc space. In another embodiment, the spinal implant can have opposed posterior and anterior sides extending between the first and second sides, and the anterior side of the spinal implant can have a height greater than a height of the posterior side such that a height of an anterior side of the disc space is greater than a height of a posterior side of the disc space.

The present invention also provides various techniques for inserting and positioning a spinal implant between adjacent vertebrae. In one embodiment, the spinal implant can be inserted through an incision formed in an anterior side of a patient's body, and the implant can be positioned such that it fills a substantial portion of the disc space. In another embodiment, the spinal implant can be inserted through an incision formed in a posterior side of a patient's body, and it can be guided into a position adjacent the concave side of the curvature of the spinal column. In yet another embodiment, the method can include inserting a second spinal implant through the incision formed in the posterior side of the patient's body, and guiding the second spinal implant into a position adjacent the convex side of the curvature of the spinal column.

In other aspects, the various methods can also include removing at least a portion of an intervertebral disc located between the adjacent vertebrae prior to inserting the spinal implant, and/or mating at least one connecting element extending longitudinally along the spinal column to the adjacent vertebrae.

In yet another embodiment, a method for correcting a spinal deformity is provided and includes inserting a wedged implant between two adjacent vertebrae located at an apex of a curvature resulting from a deformity in a spinal column. The wedged implant can be oriented such that a height between the adjacent vertebrae is increased along a concave side of the curvature to interrupt the curvature of the spinal deformity and thereby correct the spinal deformity. The implant can be inserted between the vertebrae using various approaches including a posterior approach or an anterior approach.

In yet another embodiment, the implant can be positioned into a disc space between adjacent vertebrae in a deflated configuration, and it can be inflated such that the implant has a wedge-shaped configuration with a first side having a height that is greater than a height of a second opposite side to thereby increase a height between the adjacent vertebrae along a concave side of the curvature. This allows the implant to be introduced into the disc space from a convex side of a curvature in the spinal column. In an exemplary embodiment, the implant is inflated with a material that hardens such that the inflated implant is rigid.

In other aspects, the implant can be positioned in the disc space in a first orientation in which a first side of the implant has a height that is less than a height of a second opposite side of the implant. The implant can then be adjusted into a final orientation in which the first side has a height that is greater than a height of the second opposite side to thereby increase a height between the adjacent vertebrae along a concave side of a curvature.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1A:
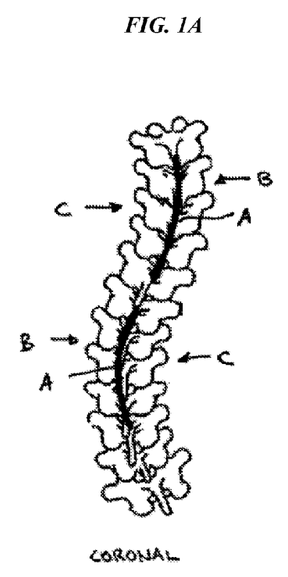
FIG. 1A is a coronal view of a spinal column showing abnormal curvatures of the spine.
Figure 1B:
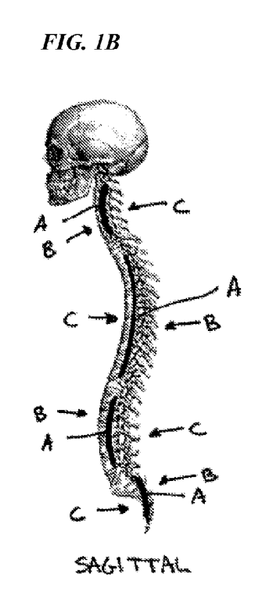
FIG. 1B is a sagittal view of the spinal column showing abnormal curvatures of the spine.
Figure 1C:
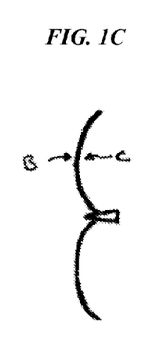
FIG. 1C is a schematic showing a curvature of the spine with a wedged implant positioned at an apex of the curvature to interrupt and correct the curvature.

The present invention generally provides methods and devices for correcting spinal deformities, and in particular for correcting an abnormal curvature in the spine. In general, various wedge-shaped implants are provided that can be used to correct a deformity. In an exemplary embodiment, one or more implants can be positioned between adjacent vertebrae located at a substantial apex of a curvature in the coronal plane of the spine to increase a height between the vertebrae on a lateral side of the disc space adjacent to the concave side of the curvature. FIG. 1A illustrates various curvatures located in the coronal plane of a spinal column. Reference A indicates the substantial apex of each curvature, reference B indicates the convex side of each curvature, and reference C indicates the concave side of each curvature. Thus, in an exemplary embodiment, at least a portion of at least one implant can be positioned between adjacent vertebrae located at a substantial apex A of a curvature in the coronal plane. The implant(s) can be positioned such that a height of the implant (s) increases in a medial-lateral direction relative to the disc space, and the maximum height of the implant is positioned adjacent to the concave side C of the curvature. This will allow the implant(s) to essentially break the curvature, thereby forming two smaller curvatures of the spine, as shown in FIG. 1C. In addition to correcting a curvature in the coronal plane, the implant(s) can also optionally correct a curvature in the sagittal plane of the spine. FIG. 1B illustrates various curvatures located in the sagittal plane, and again reference A indicates the apex of each curvature, reference B indicates the convex side of each curvature, and reference C indicates the concave side of each curvature. One or more spinal implants positioned between adjacent vertebrae located at the apex A of a curvature can have a height that increases in a posterior-anterior direction, and the maximum height of the implant can be positioned adjacent to the concave side C of the curvature to correct the curvature in the sagittal pane.

A person skilled in the art will appreciate that the various spinal implants disclosed herein are merely exemplary embodiments, and that the implants can have a variety of other configurations and features to achieve correction of a curvature in the coronal and/or sagittal planes of the spine.

Moreover, the methods and devices can be used in various regions of the spine, including the cervical, thoracic and lumbar regions of the spine.

Figure 2A:
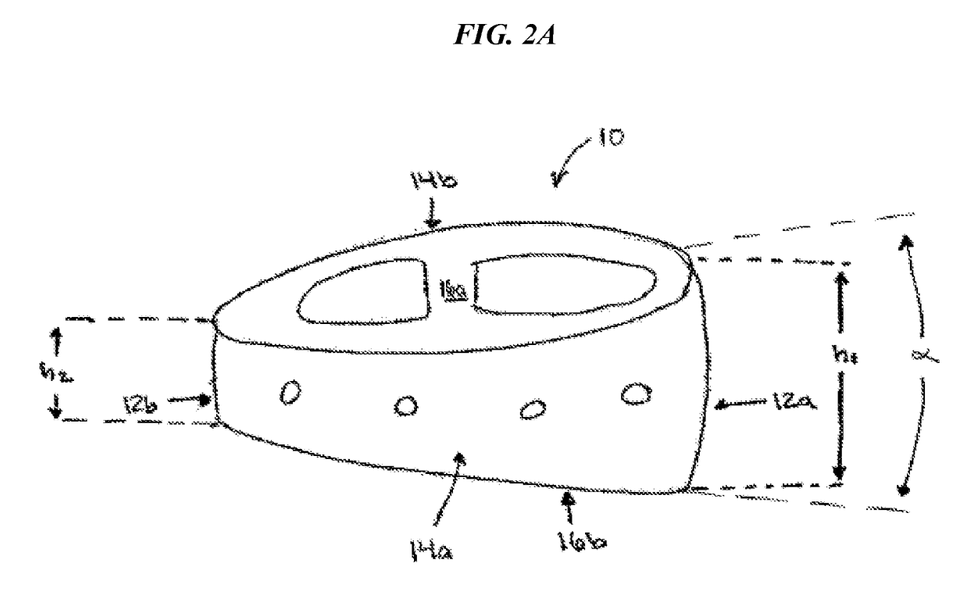
FIG. 2A is a perspective view of one embodiment of spinal implant having a medial-lateral wedge for correcting a curvature in the coronal plane of a spine.

FIG. 2A illustrates one exemplary embodiment of an intervertebral spinal implant 10. In this embodiment, the implant 10 is wedged in a medial-lateral direction to correct a deformity in the coronal plane of the spine. As shown, the spinal implant 10 generally includes a body having a disc-shaped configuration such that the implant 10 is configured to match the footprint of an endplate of a vertebra. The implant 10 can thus occupy all or at least a substantial portion of the disc space between adjacent vertebrae. As further shown, the implant 10 includes opposed first and second lateral sides 12a, 12b that are configured to be positioned adjacent to opposed lateral sides of a disc space between adjacent vertebrae. The implant 10 also includes opposed anterior and posterior sides 14a, 14b extending between the opposed first and second lateral sides 12a, 12b and configured to be positioned adjacent to posterior and anterior sides of a disc space. The sides 12a, 12b, 14a, 14b are connected by opposed superior and inferior surfaces 16a, 16b which are configured to be positioned adjacent to the endplates of adjacent superior and inferior vertebrae. As indicated above, the illustrated implant 10 can be wedged in a medial-lateral direction to correct a deformity in the coronal plane. As shown in FIG. 2A, the first lateral side 12a has a height $h_1$ that is greater than a height $h_2$ of the second lateral side 12b of the implant 10. The difference in height can vary depending on the desired degree of correction needed, but in an exemplary embodiment the height of the implant increases at an angle α in the range of about 5° to 30°.

Figure 2B:
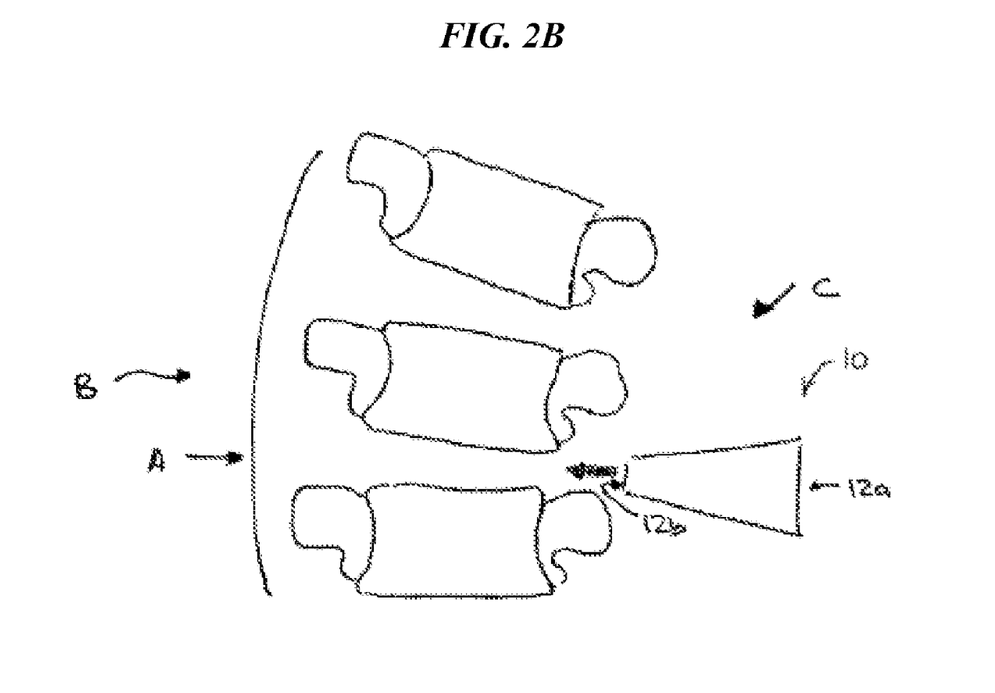
FIG. 2B is an anterior coronal view of adjacent vertebrae of a spinal column having an abnormal curvature, showing the wedge-shaped spinal implant of FIG. 2A about to be inserted between the adjacent vertebrae.
Figure 2C:
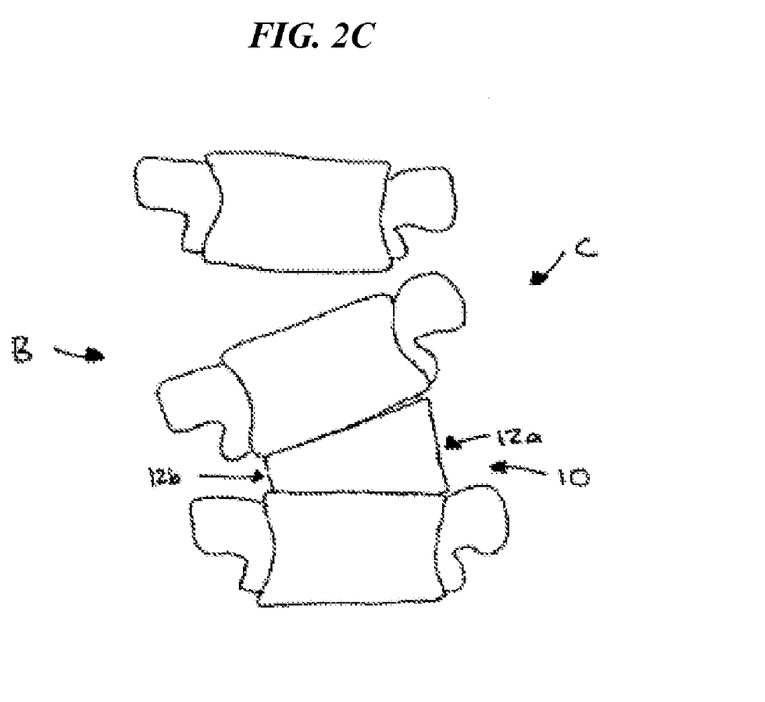
FIG. 2C is an anterior coronal view of the adjacent vertebrae and implant of FIG. 2B, showing the implant positioned between adjacent vertebrae.

In use, as shown in FIGS. 2B-2C, the wedged-shaped spinal implant 10 can be positioned between adjacent vertebrae located at a substantial apex A of a curvature in the coronal plane of the spine (shown in FIG. 1A) to interrupt the curvature and thereby correct the deformity. While various techniques known in the art can be used to introduce the implant 10 into the disc space, in one exemplary embodiment the implant 10 can be introduced using an anterior approach, also known as an anterior lumbar interbody fusion (ALIF) technique. This approach is particularly useful with implants having a shape and size that matches the footprint of an endplate of a vertebra, as the anterior approach allows for additional space to introduce the implant. In general, an incision is formed in an anterior side of a patient's body, and a pathway is formed to the adjacent vertebrae between which the implant is to be inserted. A cannula or other device can be used to form a pathway from the skin incision to the disc space. In an exemplary embodiment, the nucleus pulposus of the natural disc can be removed from the disc space, leaving a portion of the annulus fibrosus of the disc in place.

Once the disc space is prepared, the implant 10 can be passed through the pathway and oriented between two adjacent vertebrae such that the abnormal curvature is interrupted leading to correction of the spinal deformity. FIG. 2B illustrates a curvature in a coronal plane of several adjacent vertebrae of a spine, showing a convex side B of the curvature and a concave side C of the curvature. As shown in FIGS. 2B and 2C, the implant 10 is preferably introduced into the disc space located adjacent to the apex A of the curvature. In order to correct the curvature, the implant 10 is oriented such that the first lateral side 12a, i.e., the side having the maximum height, is located on the lateral side of the disc space adjacent to the concave side C of the curvature. The opposed second lateral side 12b, i.e., the side having the minimum height, is located on the opposed lateral side of the disc space adjacent to the convex side B of the curvature. As a result, the implant 10 interrupts the curvature in the coronal plane, thereby correcting the deformity, as shown in FIG. 2C. A person skilled in the art will appreciate that the height of the implant 10 can also be sufficient to restore normal height to the disc space between the adjacent vertebrae.

Figure 3:
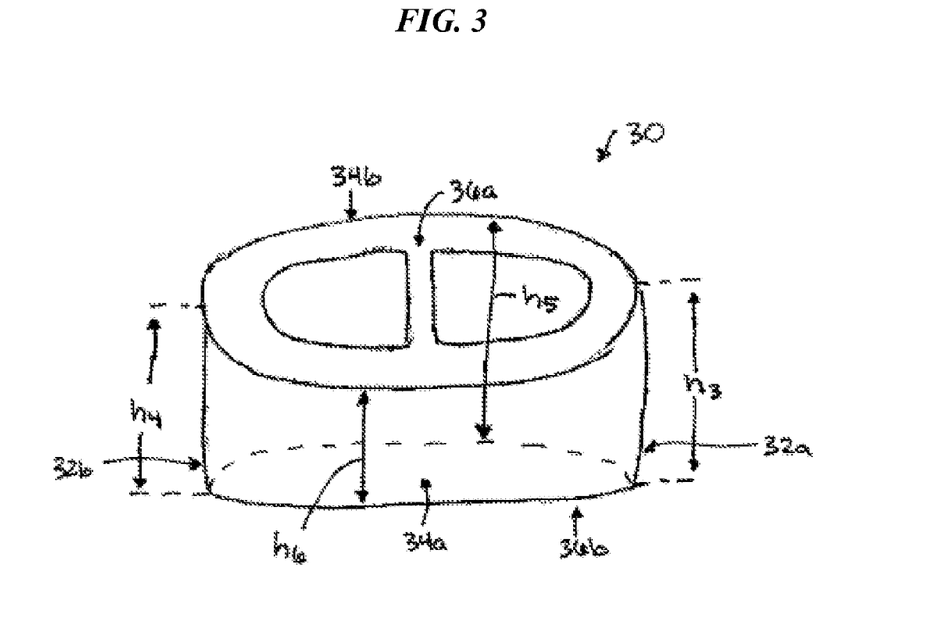
FIG. 3 is a perspective view of another embodiment of a spinal implant having a medial-lateral wedge and an anterior-posterior wedge for correcting a curvature in the coronal and sagittal planes of a spinal column.

While the implant of FIG. 2A is wedged in a medial-lateral direction to correct a curvature in the coronal plane, the implant can also optionally be wedged in the posterior-anterior direction to correct a curvature in the sagittal plane. FIG. 3 illustrates one exemplary embodiment of a spinal implant that is wedged in both the medial-lateral and posterior-anterior directions. As shown, the spinal implant 30 has a shape and size that is similar to the implant 10 of FIG. 2. In particular, the implant 30 includes first and second opposed lateral sides 32a, 32b, opposed anterior and posterior sides 34a, 34b, and opposed superior and inferior surfaces 36a, 36b. As with the implant 10 of FIG. 2, the first lateral side 32a of the implant 30 shown in FIG. 3 has a height $h_3$ that is greater than a height $h_4$ of the second lateral side 32b of the implant 30. In this embodiment, the posterior side 34b of the implant 30 also has a height $h_5$ that is greater than a height $h_6$ of the anterior side 34a of the implant 30. The implant 30 is thus wedged in both the medial-lateral direction and the posterior-anterior direction. A person skilled in the art will appreciate that the height $h_3$, $h_4$ on the lateral sides 32a, 32b will not be constant, but rather will necessarily increase from the anterior end of each lateral side 32a, 32b to the posterior end of each lateral side 32a, 32b. The height $h_5$, $h_6$ on the anterior and posterior sides 34a, 34b will likewise increase from one lateral end of each side 34a, 34b to the other lateral end of each side 34a, 34b. Thus, while each side 32a, 32b, 34a, 34b of the implant 30 is described as having a height $h_3$, $h_4$, $h_5$, $h_6$, the height is intended to refer to the height along the entire length a side of the implant.

In use, the implant 30 can be inserted between two adjacent vertebrae in a spinal column to correct curvatures in both the coronal and sagittal planes. As previously explained, the implant is preferably positioned between the vertebrae located at the apex of the curvature being corrected. Various techniques can be used for introducing the implant 30 into the disc space, but in an exemplary embodiment the implant 30 is introduced using an ALIF approach, as previously explained above. Once the implant 30 is positioned within the disc space, the implant 30 can be oriented such that the maximum height in the medial-lateral direction is positioned adjacent to the concave side of a curvature in the coronal plane, and the maximum height in the posterior-anterior direction is positioned adjacent to the concave side of the curvature in the sagittal plane. In particular, the first lateral side 32a (i.e., the medial-lateral side having the maximum height) can be positioned on the lateral side of the disc space that is adjacent to the concave side of a curvature in the coronal plane, and the second lateral side 32b can be positioned on the opposed lateral side of the disc space that is adjacent to the convex side of the curvature in the coronal plane. Where the sagittal plane is curved such that the anterior side of the disc space is located adjacent to the convex side of the curvature and the posterior side of the disc space is located adjacent to the concave side of the curvature, the posterior side 34b (i.e., the posterior-anterior side having the maximum height) can be positioned adjacent to the posterior side of the disc space and thus adjacent to the concave side of the curvature, and the anterior side 34a can be positioned adjacent to the anterior side of the disc space and thus adjacent to the convex side of the curvature. Conversely, where the sagittal plane is curved such that the anterior side of the disc space is located adjacent to the concave side of the curvature and the posterior side of the disc space is located adjacent to the convex side of the curvature, the posterior side 34b of the implant 30 can be positioned adjacent to the anterior side of the disc space and thus adjacent to the concave side of the curvature, and the posterior side 34a can be positioned adjacent to the anterior side of the disc space and thus adjacent to the convex side of the curvature. A person skilled in the art will appreciate that the terms posterior-anterior are used for reference purposes only.

Figure 4A:
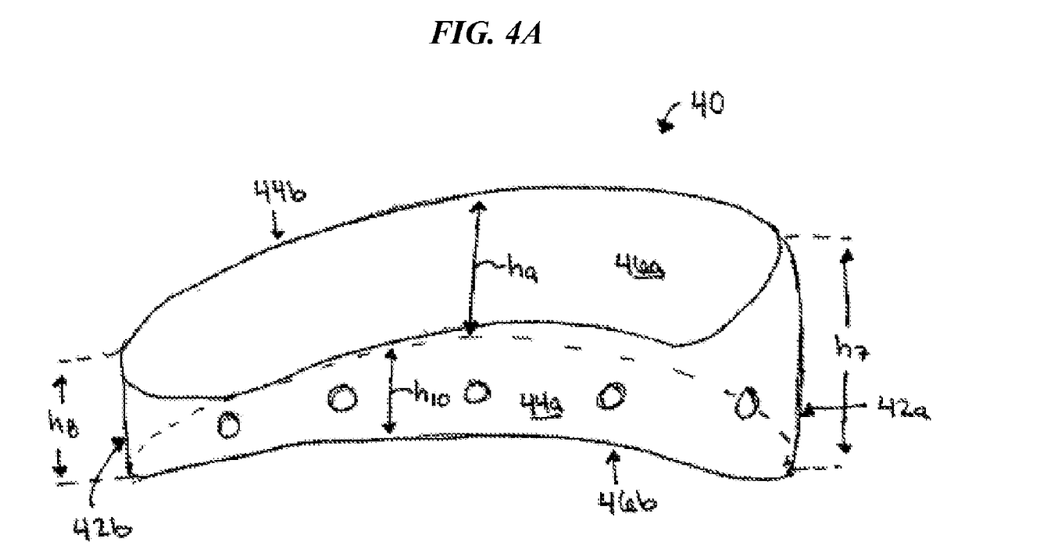
FIG. 4A is a perspective view of yet another embodiment of a spinal implant having a medial-lateral wedge and an anterior-posterior wedge for correcting a curvature in the coronal and sagittal planes of a spinal column.

FIG. 4A illustrates another exemplary embodiment of a spinal implant that is wedged in both the medial-lateral and posterior-anterior directions. As shown, implant 40 has a bean-shaped configuration. In particular, the implant 40 includes opposed anterior and posterior sides 42a, 42b, first and second opposed lateral sides 44a, 44b, and opposed superior and inferior surfaces 46a, 46b. In this embodiment, the anterior side 42a of the implant 40 has a height $h_7$ that is greater than a height $h_8$ of the posterior side 42b of the implant 40. As further shown in FIG. 4A, the second lateral side 44b of the implant 40 has a height $h_9$ that is greater than a height $h_{10}$ of the opposing first lateral side 44a of the implant 40. Therefore, the implant 40 is wedged in both the medial-lateral and posterior-anterior directions. A person skilled in the art will appreciate that the height $h_7$, $h_8$ on the anterior and posterior sides 42a, 42b will not be constant, but rather will necessarily increase from one lateral end of each side of 42a, 42b to the other lateral end of each side of 42a, 42b, and that the height $h_9$, $h_{10}$ on the lateral sides 44a, 44b will likewise increase from the anterior end of each side 44a, 44b to the posterior end of each side 44a, 44b.

In use, as shown in FIGS. 4B-4F, the spinal implant 40 can be inserted between two adjacent vertebrae located at a substantial apex A of a curvature in both the coronal (FIG. 4B) and sagittal (FIG. 4C) planes of the spine. Various techniques can be used for introducing the implant into the disc space, but in an exemplary embodiment the implant 40 can be introduced using a transforaminal lumbar interbody fusion (TLIF) approach. In general, in a TLIF approach the spinal column is accessed from the posterior side of a patient. An incision is formed in the posterior side of a patient's body, and a pathway is formed to the adjacent vertebrae between which the implant is inserted. A cannula or other device can be used to form a pathway from the skin incision to the disc space. The intervertebral disc or portions thereof can then be removed from the disc space.

Figure 4B:
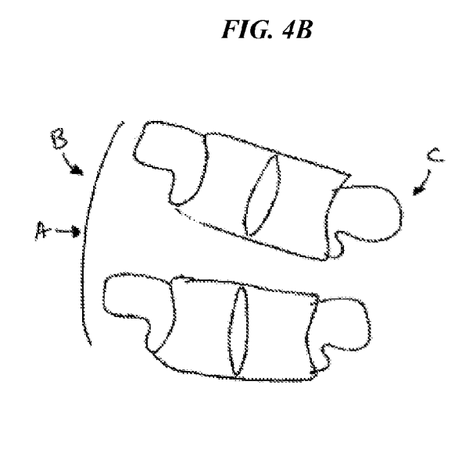
FIG. 4B is a posterior coronal view of two adjacent vertebrae of a spinal column, showing an abnormal coronal curvature.
Figure 4C:
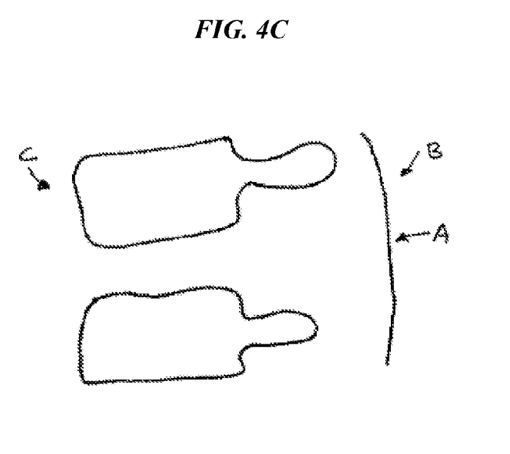
FIG. 4C is a side sagittal view of the adjacent vertebrae of FIG. 4B, showing an abnormal sagittal curvature.
Figures 4D, 4E:
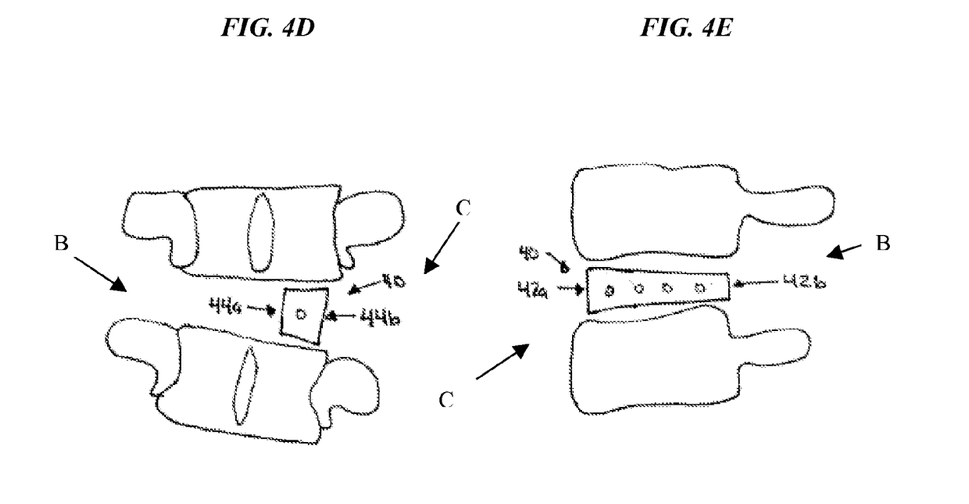
FIG. 4D is a posterior coronal view of the adjacent vertebrae of FIG. 4B, showing the spinal implant of FIG. 4A inserted between the adjacent vertebrae for correcting the coronal curvature.
FIG. 4E is a side sagittal view of the adjacent vertebrae and spinal implant of FIG. 4D, showing the spinal implant positioned to correct the sagittal curvature.
Figure 4F:
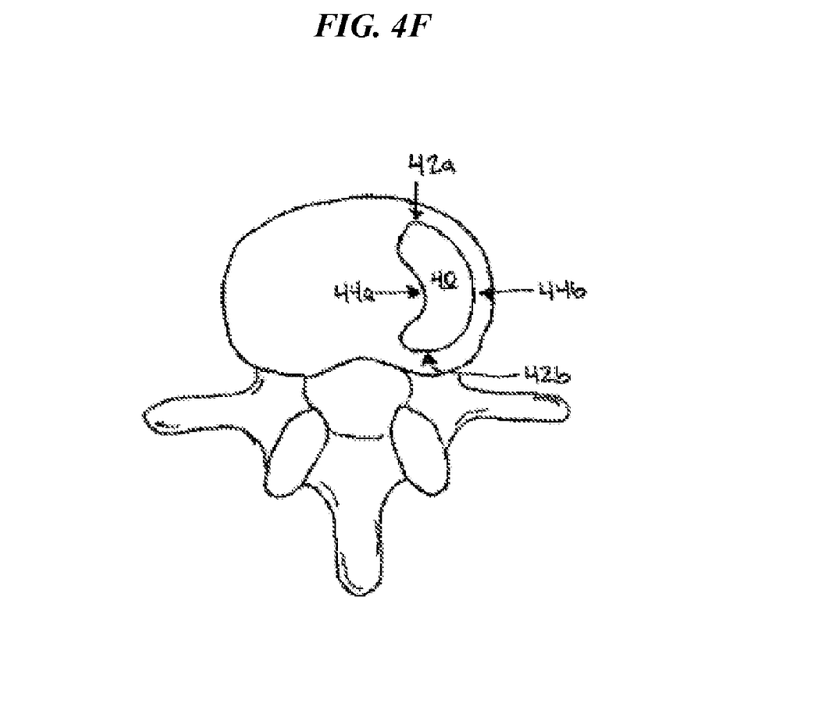
FIG. 4F is a superior view of one of the vertebrae of FIGS. 4D and 4E, showing the implant positioned on a lateral side of the disc space.

Following preparation of the disc space, the implant 40 can be inserted through the pathway across the midline or in a medial-lateral direction. The bean-shaped configuration of the implant 40 is particularly useful for guiding the implant 40 across the midline and along a curved pathway. Once inserted, the implant 40 can be oriented between two adjacent vertebrae located at the apex A of the curvature such that the abnormal curvature is interrupted, thereby correcting the spinal deformity. As illustrated in FIGS. 4B and 4D, when the abnormal curvature is in the coronal plane of the spine, the implant 40 can be oriented such that second lateral side 44b (i.e., the medial-lateral side having the greater height) is positioned on the lateral side of the disc space that is adjacent to the concave side C of the curvature, and the first lateral side 44a is facing in the direction of the convex side B of the curvature. In this embodiment, the implant 40 is configured to remain within one lateral side of the disc space. This is illustrated in FIG. 4F, which shows a top view of the spinal implant 40 positioned in the disc space of a vertebral body such that the implant 40 occupies only one lateral side of the disc space. While not shown, a second implant can optionally be implanted in the opposed lateral side of the disc space. As further shown in FIGS. 4C and 4E, the implant 40 can also correct an abnormal curvature in the sagittal plane. FIG. 4C illustrates the anterior side of the disc space located adjacent the concave side C of the curvature and the posterior side of the disc space located adjacent the convex side B of the curvature. As shown in FIG. 4E, the abnormal curvature can be corrected by orientating the implant 40 such that anterior side 42a (i.e. the anterior-posterior side having the greater height) is positioned adjacent to the anterior side of the disc space and thus adjacent to the concave side C of the curvature, and the posterior side 42b is positioned adjacent to the posterior side of the disc space and thus adjacent to the convex side B of the curvature. As a result, the implant will correct the deformity in the coronal and sagittal plane.

Figure 5A:
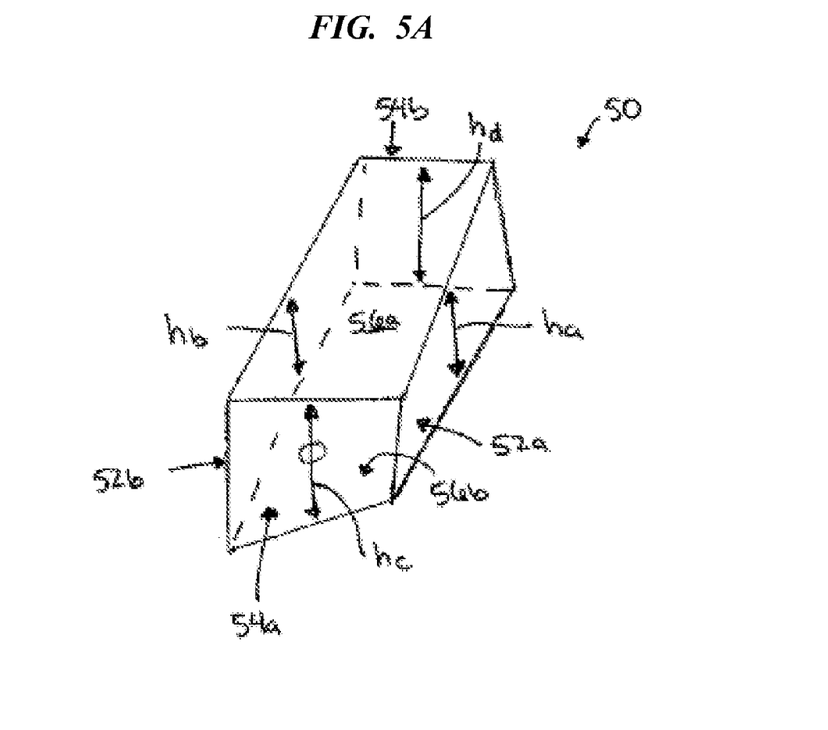
FIG. 5A is a perspective view of yet another embodiment of a spinal implant having a medial-lateral wedge and an anterior-posterior wedge for correcting a curvature in the coronal and sagittal planes of a spinal column.
Figure 5B:
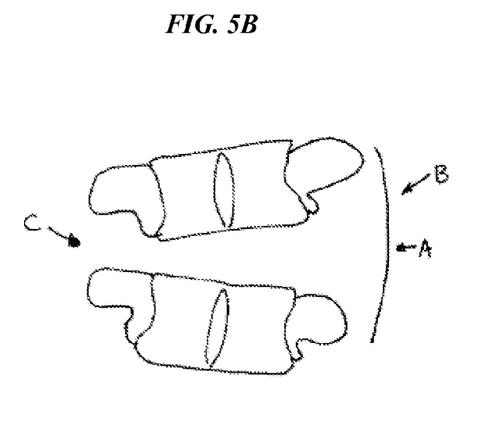
FIG. 5B is a posterior coronal view of two adjacent vertebrae of a spinal column, showing an abnormal coronal curvature.

FIG. 5A illustrates yet another exemplary embodiment of a spinal implant that is wedged in both the medial-lateral and anterior-posterior directions. In this embodiment, the implant 50 is similar to implant 40 but has a rectangular-shaped configuration. In particular, the implant 50 includes first and second opposed lateral sides 52a, 52b, opposed anterior and posterior sides 54a, 54b, and opposed superior and inferior surfaces 56a, 56b. As with the implant 40 of FIG. 4A, the second lateral side 52b of the implant 50 has a height $h_b$ that is greater than a height $h_a$ of the first lateral side 52a of the implant 50. However, in this embodiment, the posterior side 54b of implant 50 has a height $h_d$ that is greater than a height $h_c$ of the anterior side 54a of the implant 50.

Figure 5C:
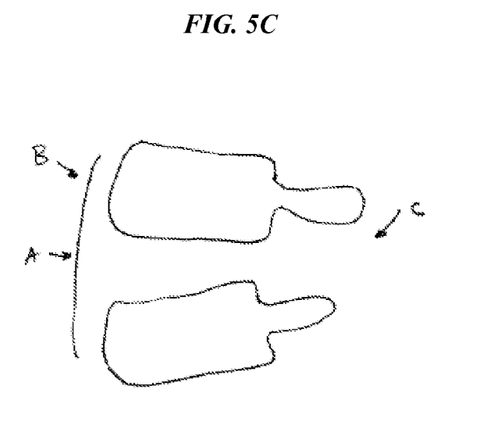
FIG. 5C is a side sagittal view of the adjacent vertebrae of FIG. 5B, showing an abnormal sagittal curvature.
Figure 5D:
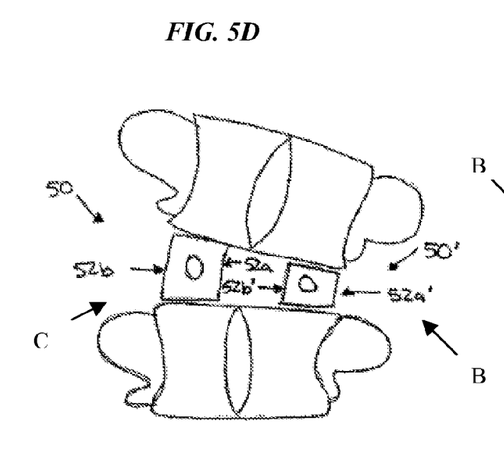
FIG. 5D is a posterior coronal view of the adjacent vertebrae of FIG. 5B, showing two implants having the configuration shown in FIG. 5A positioned between the adjacent vertebrae to correct the coronal curvature.
Figure 5E:
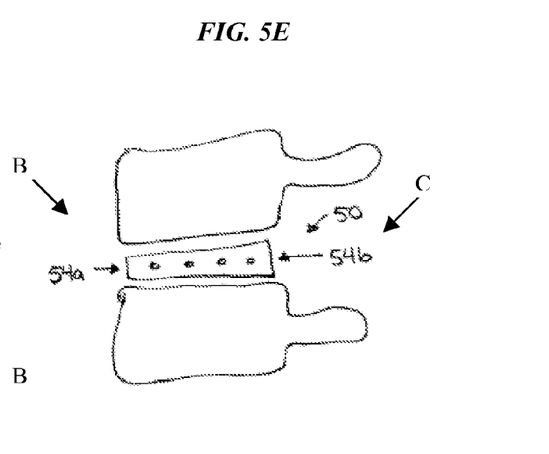
FIG. 5E is a side sagittal view of the adjacent vertebrae and spinal implants of FIG. 5D, showing the implants positioned to correct the sagittal curvature.

FIGS. 5B-5E illustrate one exemplary method for correcting a deformity in both the coronal and sagittal planes using the implant 50 of FIG. 5A. In this embodiment, a first implant 50 is positioned within a first lateral side of a disc space and a second implant 50' is positioned within a second opposed lateral side of a disc space. The implants 50, 50' are preferably positioned between the vertebrae located at the apex of the curvature being corrected. Although various techniques can be used for introducing the implants 50, 50' into the intervertebral disc space, in an exemplary embodiment the implants 50, 50' are introduced using a posterior lumbar interbody fusion (PLIF) approach. The PLIF approach is similar to the TLIF approach discussed with respect to implant 40, except that incisions are formed on each lateral side of the patient's back to allow each implant 50, 50' to be introduced along separate pathways. When the implants 50, 50' are positioned within the disc space, the implants 50, 50' can be oriented such that the greater height in the medial-lateral direction is positioned adjacent the concave side C of a curvature in the coronal plane (FIG. 5B), and the greater height in the posterior-anterior direction is positioned adjacent to the concave side C of the curvature in the sagittal plane (FIG. 5C). In particular, as illustrated in FIG. 5D, the first implant 50 can be positioned between two vertebrae located at a substantial apex A of a curvature in a coronal plane, and it can be positioned on one lateral side of the disc space. As shown, the implant 50 can be oriented such that the first lateral side 52a of the implant 50 faces the midportion of the disc space and the second lateral side 52b (i.e., the medial-lateral side having a maximum height) is positioned adjacent to the concave side C of the curvature. The second implant 50' is can be positioned between the two vertebrae in the opposed lateral side of the disc space opposite the first implant 50. The second implant 50' is likewise oriented such that the first lateral side 52a' is positioned adjacent to the convex side B of the curvature, and the second lateral side 52b' (i.e., the medial-lateral side having a maximum height) of the implant 50' faces the mid-portion of the disc space. In order to properly correct the curvature, second implant 50' preferably has an overall height (i.e., a height on each side) that is less than an overall height of the first implant 50, such that the two implants 50, 50' have a combined wedge-configuration.

As previously indicated, the implants 50, 50' can also correct a curvature in the sagittal plane. FIG. 5C illustrates the sagittal plane curved such that the anterior side of the disc space is located adjacent the convex side B of the curvature and the posterior side of the disc space is located adjacent the concave side C of the curvature. As shown in the FIG. 5E, the first implant 50 can be positioned between the vertebrae such that the anterior side 54a of the implant 50 is positioned adjacent to the anterior side of the disc space and thus adjacent to the convex side B of the curvature, and the posterior side 54b (i.e., the anterior-posterior side having a maximum height) is positioned adjacent to the posterior side of the disc space and thus adjacent to the concave side C of the curvature. While not shown, the second implant 50' can likewise be oriented to position the posterior-anterior side having the maximum height adjacent to the posterior side of the disc space, and thus adjacent to the concave side C of the curvature.

Figure 6A:
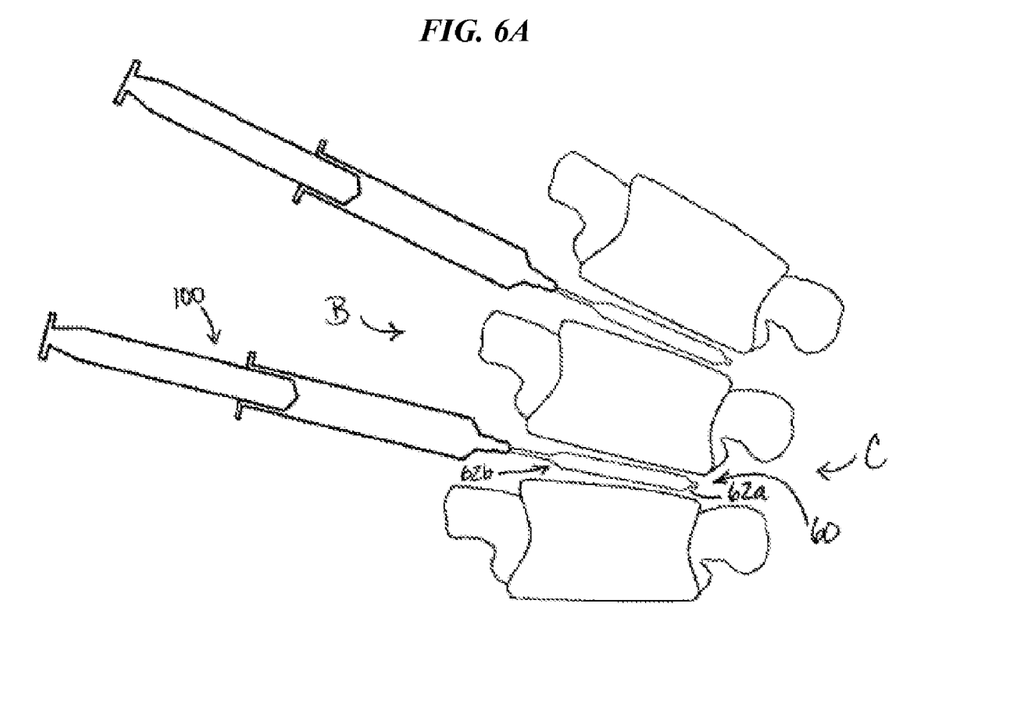
FIG. 6A is a side view of another embodiment of a spinal implant positioned between adjacent vertebrae, shown in a deflated configuration.
Figure 6B:
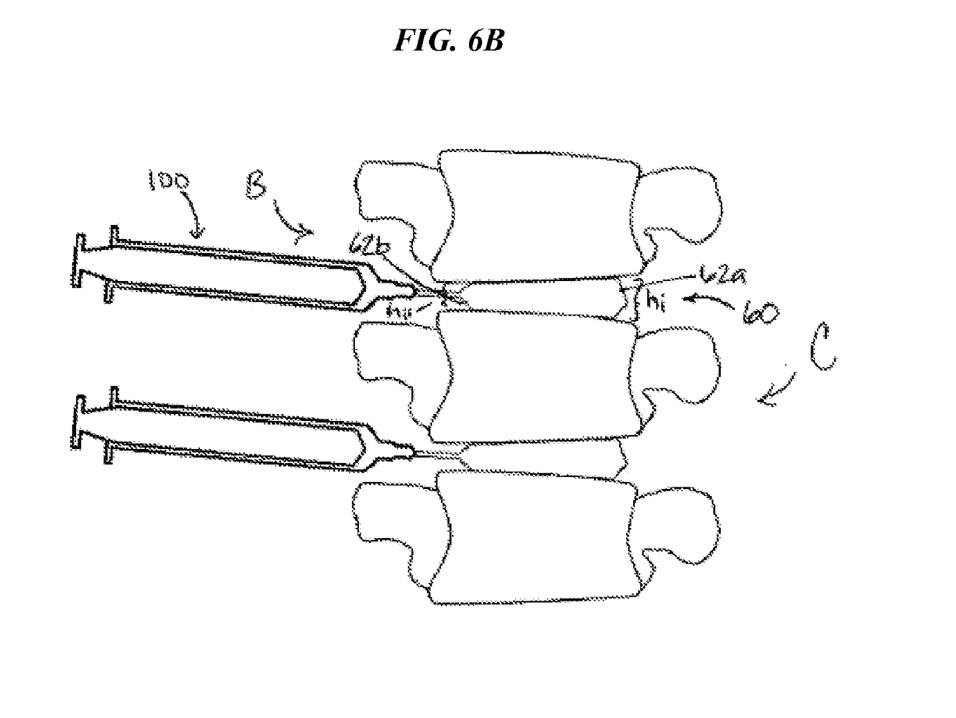
FIG. 6B is a side view of the spinal implant of FIG. 6A, shown in an inflated configuration.

FIGS. 6A-6B illustrate yet another exemplary embodiment of a spinal implant. In this embodiment, the spinal implant 60 is inflated and has a pre-formed configuration, such as, for example, a balloon. As shown, the implant 60 can have a deflated configuration (FIG. 6A), and it can be inflated such that the implant 60 has a wedged-shaped configuration (FIG. 6B). The implant 60 can also include first and second opposed lateral sides 62a, 62b, and opposed superior and inferior surfaces 64a, 64b. As further shown in FIG. 6B, when inflated, the first lateral side 62a of the implant 60 can have a height $h_i$ that is greater than a height $h_{ii}$ of the opposed second lateral side 62b of the implant 60. The implant 60 can be inflated using a variety of known inflation devices, such as, for example, a syringe 100 as shown in FIGS. 6A-6B. The implant 60 can also be inflated using a variety of materials, but preferably, to ensure that the implant 60 retains the wedge-shaped configuration once inflated, the implant 60 is filled with a material that hardens such the implant 60 becomes rigid. By way of non-limiting example, one suitable hardening material includes polymethylmethacrylate.

In use, as shown in FIGS. 6A-6B, the spinal implant 60 can be inserted between two adjacent vertebrae located at a substantial apex A of a curvature of a spinal deformity. FIGS. 6A-6B illustrate a curvature in a coronal plane of adjacent vertebrae of a spine, showing a convex side B of the curvature and a concave side C of the curvature. Various techniques can be used for introducing the implant 60 into the disc space between two adjacent vertebrae, but in an exemplary embodiment as shown in FIG. 6A, the implant 60 is preferably inserted into the disc space by accessing the convex side B of the abnormal spinal curvature. Prior to insertion of the implant 60, the intervertebral disc or portions thereof can be removed from the disc space. Following preparation of the disc space, the implant 60 can be oriented between the adjacent vertebrae in its deflated configuration and is positioned such that the first lateral side 62A, i.e., the side having the maximum height upon inflation, is located on the lateral side of the disc space adjacent to the concave side C of the curvature. The opposed second lateral side 62b, i.e., the side having the minimum height upon inflation, is located on the opposed lateral side of the disc space adjacent to the convex side B of the curvature. As shown in FIG. 6B, once the implant 60 has been introduced and properly positioned, the implant 60 can be inflated with the syringe 100 such that the implant 60 attains the wedged-shape configuration. As a result, the implant 60 interrupts the curvature in the coronal plane, thereby correcting the deformity.

Figure 7A:
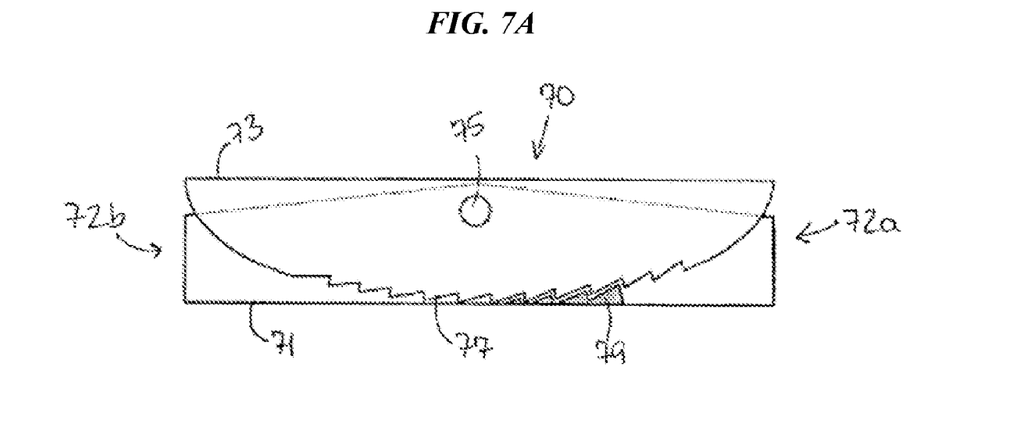
FIG. 7A is a side view of one embodiment of an adjustable spinal implant, shown in a neutral configuration.
Figure 7B:
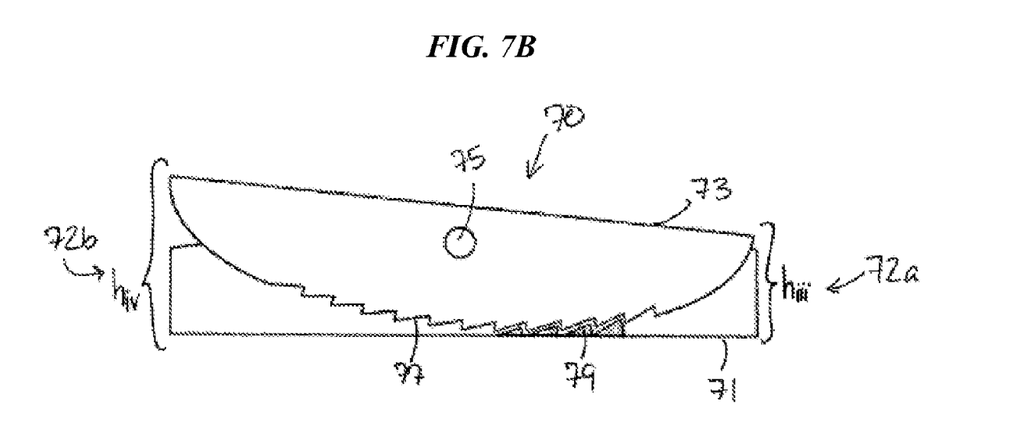
FIG. 7B is a side view of the adjustable spinal implant of FIG. 7A, shown in an initial configuration.
Figure 7C:
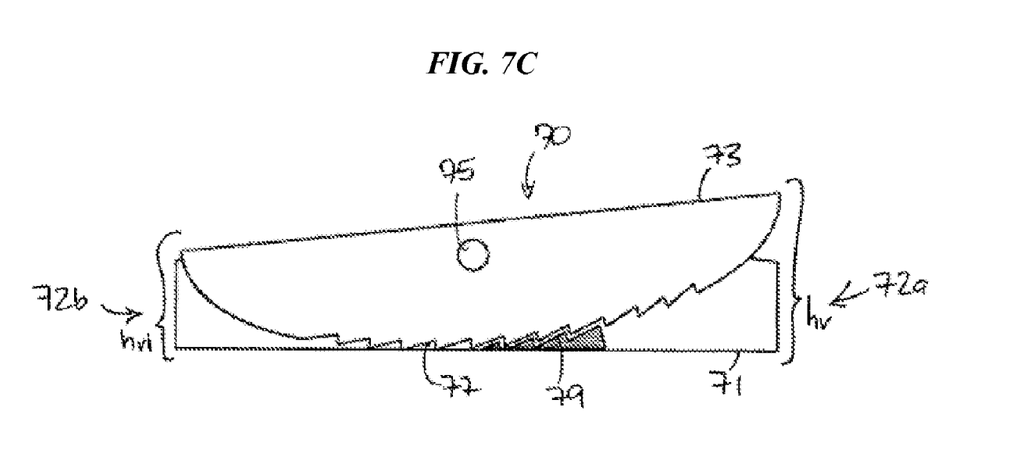
FIG. 7C is a side view of the adjustable spinal implant of FIG. 7A, shown in a final configuration.

FIGS. 7A-7C illustrate another exemplary embodiment of a spinal implant that is capable of being adjusted. As shown in FIG. 7A, in this embodiment the implant 70 can include a base 71 with a pivoting component 73 mounted thereon. The pivoting component 73 can be attached to the base 71 using, for example, a pin joint 75. In use, the pin joint 75 allows the pivoting component 73 to oscillate on the base 71 between a neutral configuration (FIG. 7A), an initial configuration (FIG. 7B), and a final configuration (FIG. 7C). The implant 70 also includes first and second opposed lateral sides 72a, 72b. Each of the lateral sides 72a, 72b can have a height that is greater than the height of the opposed lateral side depending on the position of the pivoting component 73. For example, as shown in FIG. 7B, when the pivoting component 73 is adjusted to an initial configuration, the first lateral side 72a has a height $h_{iii}$ that is less than a height $h_{iv}$ of the opposed second lateral side 72b. As illustrated in FIG. 7C, when the pivoting component 73 is configured in a final position, the first lateral side 72a can have a height $h_v$ that is greater than a height $h_{vi}$ of the opposed second lateral side 72b.

To retain the pivoting component 73 in a particular configuration, the implant 70 can further include a locking mechanism. While various locking mechanisms can be used, in one embodiment the locking mechanism can include a set of ridges 77 formed on a surface of the pivoting component 73 and a set of corresponding grooves 79 formed on a surface of the base 71. The ridges 77 mate with grooves 79 such that the pivoting component 73 is locked into a position on base 71. In use, in order to adjust the position of the pivoting component 73, a ratcheting mechanism 200 (FIG. 7E) can be used to engage and manipulate the pivoting component 73 by, for example, tensioning the pivoting component 73 from the initial configuration to the final configuration.

Figure 7D:
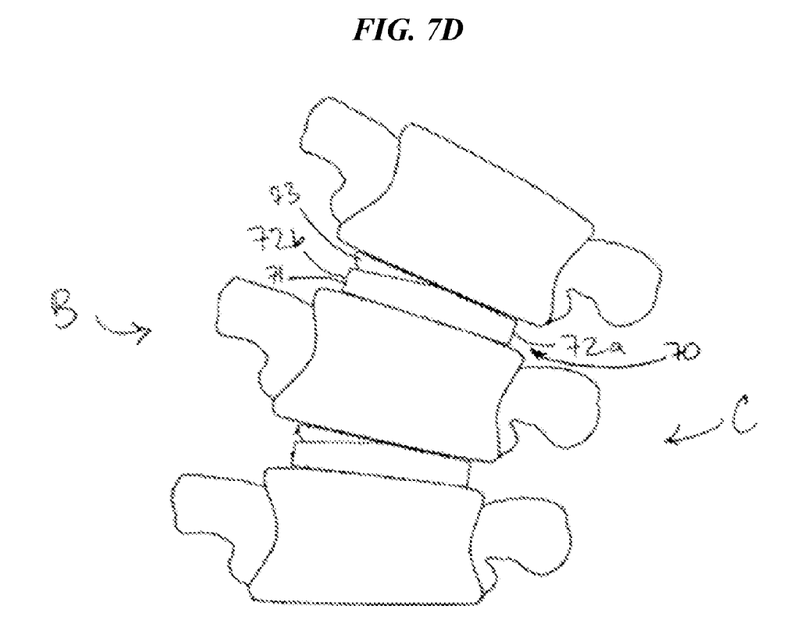
FIG. 7D is a side view of the adjustable spinal implant of FIG. 7A positioned between adjacent vertebrae, shown in an initial configuration.
Figure 7E:
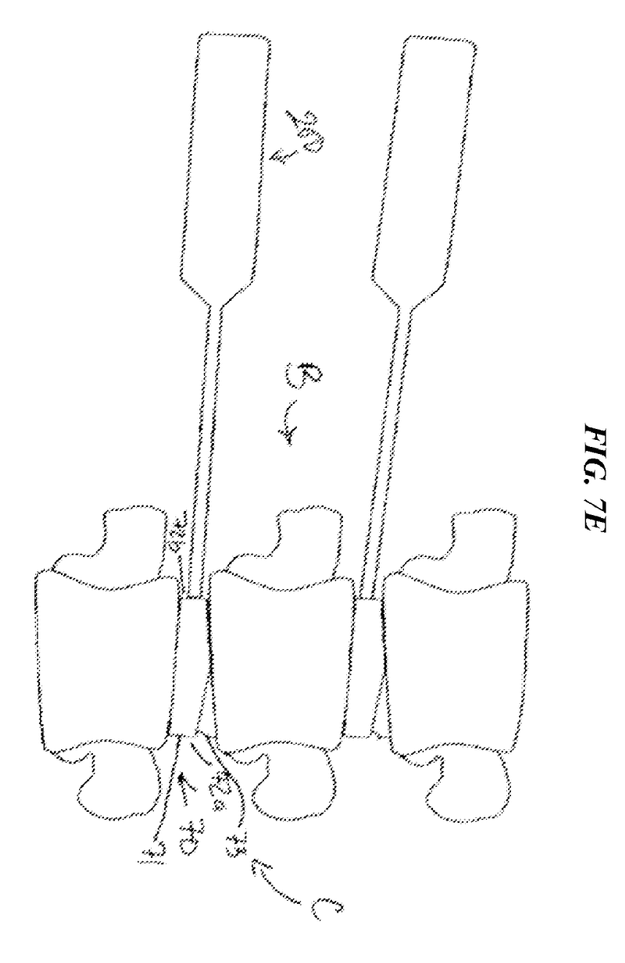
FIG. 7E is a side view of the adjustable spinal implant of FIG. 7A, shown in a final configuration.

FIGS. 7D-7E illustrate an exemplary method for correcting a curvature deformity in a coronal plane of a spinal column using the implant 70 of FIGS. 7A-7C. In this embodiment, the implant 70 can be introduced into the intervertebral disc space between two adjacent vertebrae, with the pivoting component 73 of the implant 70 located in the initial position (FIG. 7D), such that the minimum height, i.e., the first lateral side 72a, is introduced first into the disc space with the second lateral side 72b trailing. The implant 70 can then be adjusted to a final position (FIG. 7E), thereby correcting the abnormal spinal curvature. Although various techniques can be used for introducing the implant 70 into the disc space, in an exemplary embodiment the implant 70 can be introduced by accessing the spinal column in a lateral direction on a convex side of a curvature. As shown in FIG. 7D, the implant 70 can be inserted into a disc space in the initial configuration such that the first lateral side 72a has a lower height than the opposed second lateral side 72b. The implant 70 is oriented in the disc space such that the first lateral side 72a is adjacent to the concave side C of the curvature, and the second lateral side 72b is adjacent to the convex side B of the curvature. As illustrated in FIG. 7E, following the insertion of the implant 70 within the intervertebral disc space, the ratcheting mechanism 200 can be used to adjust the pivoting component 73 of the implant 70 from the initial configuration to the final configuration such that the first lateral side 72a has a height that is greater than a height of the opposed second lateral side 72b. As a result, the height along the concave side C of the curvature is increased, thus interrupting the abnormal curvature and thereby correcting the spinal deformity.

A person skilled in the art will appreciate that the various implants disclosed herein can be oriented in various directions, other than those illustrated, to achieve the desired results. In particular as previously explained, the use of the terms posterior and anterior are merely provided for convenience and do not limit the implant to being oriented such that the posterior side is located adjacent to the posterior side of the disc space and the anterior side is located adjacent to the anterior side of the disc space. The implant can be oriented in various positions within the disc space and relative to the curvature to achieve correction. In an exemplary embodiment, however, the side of the implant having the maximum height (i.e., a height greater than the opposed side) is positioned adjacent to the side of the disc space located on the concave side of the curvature.

The various implants disclosed herein can be formed from a variety of materials, and they can include various other features. For example, the implants can be made from any suitable biocompatible material such as bone, metal, metal alloys, plastics, and/or carbon fiber. In another example, the implants can have a solid structure with openings or bores, or a skeletal frame. The openings and skeletal frame permit various substances to be introduced into the implants, such as, for example, osteobiologics and bone growth promoting factors. Alternatively, the implants can be coated with such substances to promote fusion of the implants with the vertebrae between which the implants are interposed. In yet another example, the implants can include a variety of surface features for engaging the endplates of the vertebrae. Such surface features can include for example, spikes, serrations, and/or ridges.

The implants can also be provided as a kit. The kit can include a plurality of intervertebral wedged implants. Each implant can include a body have an upper surface and an opposed lower surface, opposed first and second ends that extend between the upper and lower surfaces, and first and second sides extending between the upper and lower surfaces and the first and second ends. In one embodiment, the upper and lower surfaces of the implants can be oriented at an angle relative to one another, and in an exemplary embodiment the angle of each implant can vary by increments of about 5° to 30°. In another embodiment, the first end of each implant can have a height that is greater than a height of the opposed second end, and/or the first side of each implant can have a height that is greater than a height of the opposed second side. The difference in height between the first and second ends and/or the first and second sides can define an angle, and in an exemplary embodiment the angle of each implant can vary by about 5° to 30°.

Figure 8:
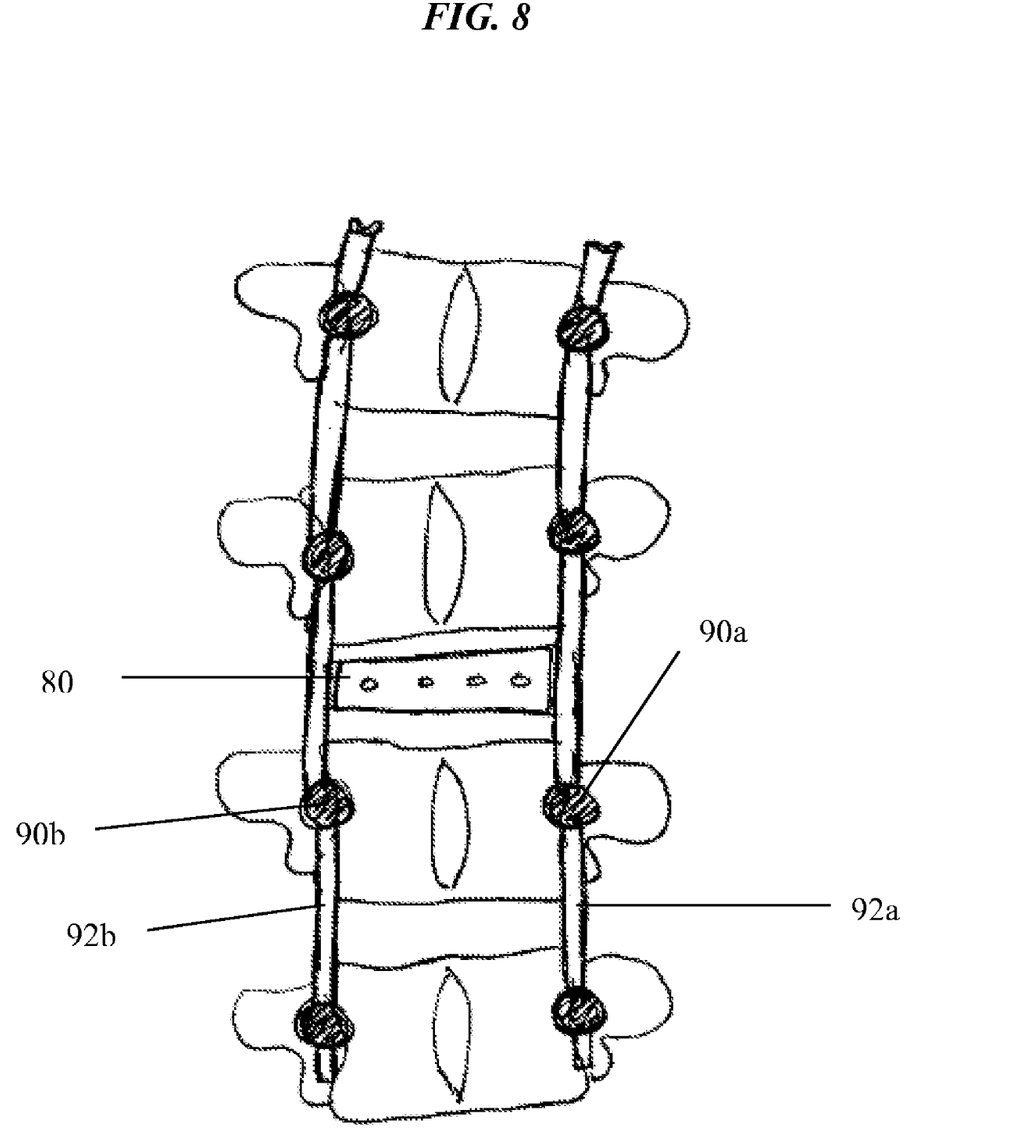
FIG. 8 is posterior view of a portion of a spinal column, showing an implant positioned between two adjacent vertebrae and showing first and second spinal fixation elements coupled to the adjacent vertebrae.

In an exemplary embodiment, the various implants discussed herein can be used in combination with a spinal fixation construct. For example, one or more implants can be positioned at one or more levels of the spine, as previously described. Once the curvature is corrected, a spinal fixation system can be implanted in the spine to maintain the vertebrae in the correct orientation. FIG. 8 illustrates a spinal implant 80 positioned between two adjacent vertebrae, and a spinal fixation system fixedly mated to a posterior side of the spinal column and extending longitudinally along lateral sides of adjacent vertebrae. The spinal fixation system generally includes first and second bone anchors 90a, 90b implanted in opposed lateral sides or each vertebra, and first and second spinal rods 92a, 92b seated within the bone anchors and extending longitudinally along opposed lateral sides of the spine. The spinal fixation system provides enhanced stability and reinforces the correction of the abnormal spinal curvature provided by the spinal implants of the present invention. A person skilled in the art will appreciate that the system can include only one fixation rod extending along one lateral side of the spine, and that various other fixation systems and techniques known in the art can be used.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for correcting a spinal deformity, comprising:
   selecting two or more spinal implants from a plurality of spinal implants, each implant having a wedge-shaped configuration with a first side having a height that is greater than a height of a second opposite side, a difference in height between the first and second sides defining an angle;
   inserting the two or more selected spinal implants into two or more disc spaces formed between pairs of adjacent vertebrae at two or more levels of a spinal column located along a curvature in a coronal plane of the spinal column resulting from a deformity in the spinal column, each implant being disc-shaped such that it has a footprint that substantially matches a footprint of a vertebral endplate, and each disc space including a first lateral side located adjacent to a concave side of the curvature in the spinal column and a second lateral side located adjacent to a convex side of the curvature in the spinal column; and
   positioning the first side of each spinal implant adjacent the first lateral side of each disc space such that a height of the first lateral side of the disc space is greater than a height of the second lateral side of the disc space to correct the curvature in the coronal plane.

2. The method of claim 1, wherein the second opposite side of each spinal implant is positioned adjacent the second lateral side of each disc space.

3. The method of claim 1, wherein the spinal column has a curvature in a sagittal plane resulting from a deformity in the spinal column, and at least one of the two or more spinal implants has opposed posterior and anterior sides extending between the first and second sides, the posterior side having a height greater than a height of the anterior side such that a height of a posterior side of the disc space is greater than a height of an anterior side of the disc space to correct the curvature in the sagittal plane.

4. The method of claim 1, wherein the spinal column has a curvature in a sagittal plane resulting from a deformity in the spinal column, and at least one of the two or more spinal implants has opposed posterior and anterior sides extending between the first and second sides, the anterior side having a height greater than a height of the posterior side such that a height of an anterior side of the disc space is greater than a height of a posterior side of the disc space to correct the curvature in the sagittal plane.

5. The method of claim 1, wherein at least one of the two or more spinal implants is inserted through an incision formed in an anterior side of a patient's body, and is positioned such that the implant fills a substantial portion of the disc space.

6. The method of claim 1, wherein at least one of the two or more spinal implants is inserted through an incision formed in a posterior side of a patient's body, and is guided into a position adjacent the concave side of the curvature of the spinal column.

7. The method of claim 1, further comprising removing at least a portion of an intervertebral disc located between the adjacent vertebrae prior to inserting at least one of the two or more spinal implants.

8. The method of claim 1, further comprising mating at least one connecting element extending longitudinally along the spinal column to the adjacent vertebrae.

9. The method of claim 1, wherein at least one of the two or more implants is inserted by positioning at least one implant in a deflated configuration into the disc space, and inflating the implant into an inflated configuration such that the implant has a wedge-shaped configuration with a first side having a height that is greater than a height of a second opposite side.

10. The method of claim 9, wherein at least one implant is inflated with a material that hardens such that the inflated implant is rigid.

11. The method of claim 1, wherein at least one of the two or more implants by positioning the implant in a first orientation in which the first side has a height that is less than a height of the second opposite side, and adjusting the implant into a final orientation in which the first side has a height that is greater than a height of the second opposite side.

12. The method of claim 1, wherein the angle of at least one of the plurality of implants varies from the angle of at least one other of the plurality of implants.

13. The method of claim 1, wherein the angle of at least one of the plurality of implants varies from the angle of at least one other of the plurality of implants by increments in the range of about 5 degrees to about 30 degrees.

14. The method of claim 1, wherein at least one of the two or more spinal implants is inserted between the adjacent vertebrae using a lateral approach.

15. A method for correcting a spinal deformity, comprising:
   selecting two or more disc-shaped wedged implants from a plurality of wedged implants;
   inserting the two or more wedged implants into two or more disc spaces formed between pairs of adjacent vertebrae located at two or more levels of a spinal column such that each implant occupies a substantial portion of each disc space; and
   orienting the two or more wedged implants such that a height between the adjacent vertebrae is increased along a concave side of the curvature to interrupt the curvature of a spinal deformity and thereby correct the spinal deformity.

16. The method of claim 15, wherein at least one of the two or more wedged implants is inserted between the adjacent vertebrae using a posterior approach.

17. The method of claim 15, wherein at least one of the two or more wedged implants is inserted between the adjacent vertebrae using an anterior approach.

18. The method of claim 15, further comprising removing at least a portion of an intervertebral disc between the adjacent vertebrae prior to inserting at least one of the two or more wedged implants.

19. The method of claim 15, further comprising mating at least one connecting element extending longitudinally along the spinal column to the adjacent vertebrae.

20. The method of claim 15, wherein inserting at least one of the two or more wedged implant comprises positioning the wedged implant in a deflated configuration between two adjacent vertebrae, and inflating the wedged implant into an inflated configuration such that the a height between the adjacent vertebrae is increased along a concave side of the curvature.

21. The method of claim 20, wherein at least one of the two or more implants is inserted on a convex side of the curvature.

22. The method of claim 15, wherein inserting at least one of the two or more wedged implants comprises positioning the wedged implant in a first orientation in which a first side has a height that is less than a height of a second opposite side, and adjusting the wedged implant into a final orientation in which the first side has a height that is greater than a height of the second opposite side to increase a height between the adjacent vertebrae along the concave side of the curvature.

23. The method of claim 15, wherein at least one of the two or more wedged implants is inserted between the adjacent vertebrae using a lateral approach.

\* \* \* \* \*